US011473078B2

(12) United States Patent
Niesert et al.

(10) Patent No.: US 11,473,078 B2
(45) Date of Patent: Oct. 18, 2022

(54) ARTIFICIAL NON-RIBOSOMAL PEPTIDE SYNTHETASES

(71) Applicant: MERCK PATENT GMBH, Darmstadt (DE)

(72) Inventors: Claus-Peter Niesert, Seeheim-Jugenheim (DE); Helge B. Bode, Oberursel (DE); Kenan Bozhueyuek, Frankfurt am Main (DE); Florian Fleischhacker, Friedberg (DE)

(73) Assignee: JOHANN WOLFGANG GOETHE-UNIVERSITAT, Frankfurt am Main (DE)

( * ) Notice: Subject to any disclaimer, the term of this patent is extended or adjusted under 35 U.S.C. 154(b) by 597 days.

(21) Appl. No.: 15/750,415

(22) PCT Filed: Jul. 6, 2016

(86) PCT No.: PCT/EP2016/001158

§ 371 (c)(1),
(2) Date: Feb. 5, 2018

(87) PCT Pub. No.: WO2017/020983

PCT Pub. Date: Feb. 9, 2017

(65) Prior Publication Data

US 2018/0230449 A1 Aug. 16, 2018

(30) Foreign Application Priority Data

Aug. 5, 2015 (EP) .................................... 15002340

(51) Int. Cl.

| | |
|---|---|
| ***C40B 40/08*** | (2006.01) |
| ***C12N 9/00*** | (2006.01) |
| ***C40B 40/06*** | (2006.01) |
| ***C12N 15/10*** | (2006.01) |
| ***C12P 21/02*** | (2006.01) |

(52) U.S. Cl.

CPC ........... *C12N 9/93* (2013.01); *C12N 15/1093* (2013.01); *C12P 21/02* (2013.01); *C12Y 603/02* (2013.01); *C40B 40/06* (2013.01); *C40B 40/08* (2013.01)

(58) Field of Classification Search

None

See application file for complete search history.

(56) References Cited

U.S. PATENT DOCUMENTS

2010/0048422 A1* 2/2010 Walsh .................. C12N 15/102 506/16

2010/0297751 A1 11/2010 Marahiel

FOREIGN PATENT DOCUMENTS

WO 2001030985 A1 5/2001

OTHER PUBLICATIONS

GenBank accession No. DQ075244 downloaded Jul. 28, 2020.*

GenBank accession No. AAZ03552 downloaded Apr. 1, 2021.*

Yamanaka et al. (PNAS 111:1957-62) (Year: 2014).*

International Search Report PCT/EP2016/001158 dated Sep. 9, 2016.

Tooming-Klunderud Ave et al: "Structural analysis of a non-ribosomal halogenated cyclic peptide and its putative operon from Microcystis: implications for evolution of cyanopeptolins.", Microbiology (Reading, England) May 2007, vol. 153, No. Pt 5, May 2007 (May 1, 2007), pp. 1382-1393.

Database GenBank [online] Apr. 26, 2007 (Apr. 26, 2007), Tooming-Klunderud,A., et al.: "McnC [*Microcystis* sp. NIVA-CYA 172/5].", XP002761184, Database accession No. AAZ03552.1.

Database GenBank [online] Apr. 3, 2013 (Apr. 3, 2013), Rokni-Zadeh,H et al.: "putative pyoverdine non-ribosomal peptide synthetase [Pseudomonas fluorescens].", XP002761185, Database accession No. AFZ61508.1.

Rokni-Zadeh Hassan et al: "Distinct lipopeptide production systems for WLIP (white line-inducing principle) in Pseudomonas fluorescens and Pseudomonas putida.", Environmental Microbiology Reports Feb. 2013, vol. 5, No. 1, Feb. 2013 (Feb. 1, 2013), pp. 160-169, XP002761186, ISSN: 1758-2229.

Marahiel M A et al: "Modular ppetide synthetases involved in nonribosomal peptide synthesis", Chemical Reviews, American Chemical Society, US, vol. 97, No. 7, Nov. 1, 1997 (Nov. 1, 1997), pp. 2651-2673, XP002133489, ISSN: 0009-2665.

Bradleys Evans et al: "Directed Evolution of the Nonribosomal Peptide Synthetase AdmK Generates New Andrimid Derivatives InVivo", Chemistry and Biology, Current Biology, London, GB, vol. 18, No. 5, Mar. 7, 2011 (Mar. 7, 2011), pp. 601-607, XP028217515, ISSN: 1074-5521, [retrieved on Mar. 28, 2011].

M. Winn et al: "Recent advances in engineering nonribosomal peptide assembly lines", Natural Product Reports, vol. 33, No. 2, Jan. 1, 2016 (Jan. 1, 2016), GB, pp. 317-347, XP055297369, ISSN: 0265-0568.

* cited by examiner

*Primary Examiner* — Christopher M Gross

(74) *Attorney, Agent, or Firm* — Millen White Zelano & Branigan, PC; Brion P. Heaney

(57) ABSTRACT

The present invention concerns a novel method for the modification and/or custom-made design of artificial non-ribosomal peptide synthetases (NRPSs) from naturally available NRPSs. The artificial NRPSs are of predetermined length and amino acid composition and sequence. Via fusion of well-defined NRPS units (so-called "exchange units") in a certain manner, using a specific sequence motif in the linker areas it is possible to construct artificial and/or modified NRPS assembly lines, which have the ability of synthesizing peptides of a desired structure.

22 Claims, 6 Drawing Sheets

Specification includes a Sequence Listing.

*De novo*

V L F L L

ARTIFICIAL NON-RIBOSOMAL PEPTIDE SYNTHETASES

SEQUENCE LISTING

The instant application contains a Sequence Listing which has been submitted electronically in ASCII format and is hereby incorporated by reference in its entirety. Said ASCII copy, created on Oct. 12, 2021, is named Boehmerm-0013_ST25 and is 361 bytes in size.

BACKGROUND OF THE INVENTION

Non-ribosomal peptide synthetases (NRPSs) and polyketide synthases (PKSs) are multifunctional enzyme complexes harboring a modular architecture (Marahiel 1997). Numerous natural products synthesized by these enzyme classes are of pharmaceutical and/or biotechnological interest because of its medicinally relevant properties including antimicrobial (e.g. teixobactin), antitumor (e.g. bleomycin), antifungal (fengycin) and immunosuppressant (cyclosporin) activity (Ling et al. 2015, Ishizuka et al. 1967, Loeffler et al. 1986, Emmel et al. 1989). Although the peptidic compounds produced by NRPSs exhibit a broad range of bioactivity and a great structural variety (e.g. non-proteinogenic amino acids, N-methylation, epimerization, heterocycies), a common mode of synthesis is shared, the so called "multiple-carrier thiotemplate mechanism".

The structure of NRPSs is obligate modular (FIG. 1). A module is defined as the catalytic unit that incorporates one specific building block (e.g. amino acid) into the growing peptide chain (Marahiel 1997). NRPS modules can be subdivided into domains and each domain is responsible for a certain reaction step within peptide assembly. For example, a canonical elongation module is composed of three domains:

An adenylation (A) domain which selectively determines and activates substrates (usually amino-acids) as an amino acyl adenylate.

A peptidyl carrier protein (PCP), also called thiolation domain (T) binds the cofactor 4-phosphopantethein, to which the activated amino acid (AA) is covalently bound by thioester formation.

A condensation (C) domain catalyzes peptide bond formation between the downstream and upstream located aminoacyl or peptidyl residues.

The first (N-terminal) module (start module) of a NRPS module often possesses no C domain and the last (C-terminal) module (termination module) usually contains a thioesterase (TE) domain (Marahiel et al. 1997). The TE domain usually is responsible for the release of linear (transfer to a water molecule), cyclic or branched cyclic peptides (amide or ester linkage). In addition to these "standard domains" (C, A, T, TE) a cyclization (Cy) domain instead of a C domain and a terminal condensation (Cterm) domain in place of a TE domain can be present. Furthermore modification domains like an epimerization (E) domain, N-methylation (MT) domain or oxidation (Ox) domain can be included in the modules.

For further general information on NRPSs and PKSs see Cane et al. (1998), Marahiel (1997), Sieber and Marahiel (2005) and Smith and Tsai (2007).

Non-ribosomal peptides (NRPs) and polyketides (PKs) are classes of secondary metabolites produced in a variety of organisms. Many members from this classification of natural products exhibit medicinally relevant properties including antimicrobial (e.g., vancomycin and erythromycin), antitumor (e.g., bleomycin and epothilone), antifungal (e.g., soraphen and fengycin), immunosuppressant (e.g., cyclophilin and rapamycin) and cholesterol-lowering (e.g., lovastatin) activity. Although NRP and PK natural products are chemically diverse, these types of compounds are biosynthesized in their cognate producer organisms in a similar manner by multienzymatic megacomplexes known as non-ribosomal peptide synthetases and polyketide synthases. These large proteins construct the framework of NRPs and PKs in an assembly-line fashion from simple chemical monomers (amino acids in the case of NRPSs, and acyl-CoA thioesters in the case of PKSs). For more information on classification of NRPs and PKs, see Cane et al. (1998) and references therein.

The power of NRPs and PKs as potential drugs lies in their diverse and complicated chemical structures. Generally, it is the intricacy of these natural products that makes them (or variants thereof) difficult to access synthetically. Several examples exist where laborious synthetic routes have been developed, rarely successfully, for NRPs or PKs. Additionally, various moieties on such molecules are inaccessible to modification by organic synthesis, or can only be produced at low yields using such techniques. This difficulty in synthesis and modification of the NRP and PK natural products underscores the need for alternative strategies to enhance synthesis and create variants of these molecules.

Despite the apparent modular structure of the NRPSs, it has, prior to present invention, in practice been difficult to swap domains so that the resulting NRPS is active. Substitution of one domain for another generally yields great (e.g., >10-fold) reductions in yield and results in increase in production of undesirable biosynthetic side products. These changes may be a result of disruptions of inter-domain quarternary interactions and therefore domain swapping requires great knowledge of the specific NRPS quarternary structure of the protein to be modified. Thus, there is a need for new methods to produce novel varieties NRPs and PKs and a need for methods that increase the yields of such NRPs and PKs.

The following domains may be included within a NRPS: C (condensation), Cy (heterocyclization), A (adenylation), T (thiolation) or PCP (peptidyl carrier protein), TE (thioesterase), E (epimerization), MT (methyltransferase), Ox (oxidase), and Re (reductase) domains.

Nonribosomal peptide synthetases generally have the following structure: A-T-(C-A-T)n-TE where A-T is the initiation module, C-A-T are the elongation modules, and TE is the termination module (FIG. 1). Within the individual modules, the following variations may, for example, occur: C is replaced by Cy, and E, MT, Ox, or Re are inserted; TE is replaced by C or Re. A complete assembly line may have an initiation module, a termination module, and somewhere between zero and n−2 elongation modules, where n is the number of monomers in the polymeric product. Exceptions to this rule may exist; e.g., the enterobactin synthetase, in which the TE domain acts as an oligomerase, so although it only has two modules, it hooks three of these dimeric products together to form a hexameric peptide product.

The NRPS core domains include the A and PCP (or T) domains (FIG. 2). This figure shows how a monomer is attached (using ATP) to the T domain of a module. In the elongation step, the monomer is transferred from the T domain of one module to the T domain of the next module. This transfer involves the C domain of the elongation module. The final step of NRP synthesis is performed by the TE domain, which catalyzes a hydrolysis, a macro-cyclization, or oligomerization reaction (FIG. 3). NRPSs are generally modular, and the series of catalytic steps moves from the amino to carboxy terminus of each polypeptide that makes up the NRPS. For example the NRPS that produces typrocidine is made of three genes producing three polypeptides. TycA contains the initiation module; TycB contains three elongation modules, and TycC contains six additional elongation modules plus a termination module. The following domains may be included within a PKS: KS (ketosynthase), AT (acyltransferase), T (thiolation), KR (ketoreductase), DH (dehydratase), ER (enoylreductase), TE (thioesterase). PKSs generally have the following structure: AT-T-(KS-AT-T)$_n$-TE. AT-T is the initiation module, KS-AT-T are the elongation modules, and TE is the termination module. The structure of a PKS is very similar to NRPS structure. There are many examples (e.g., yersiniabactin, epothilone, bleomycin) of hybrid PKS-NRPS systems in which both types of assembly line are pieced together to form a coherent unit. Within each PKS module, one either finds a KR, a KR and DH, a KR and DH and ER, or no additional domains. These extra domains within a module determine the chemical functionality at the beta carbon (e.g., carbonyl, hydroxyl, olefin, or saturated carbon).

PRIOR ART

Since 1995, when Marahiel et al. (WO200052152) were able to show that it is possible to recombine NRPSs through exchanging adenylation-thiolation didomains, NRPS research came into focus (Marahiel et al. 1995). During the last two decades, there have been a lot of attempts to reprogram NRPSs. Based on the crystal structure of the phenylalanine activating domain PheA (PDB-ID: 1 AMU) Stachelhaus et al. were able to elucidate the specificity conferring AAs in the catalytic center (Conti et al. 1997, Stachelhaus et al. 1999). With this specificity conferring code, denoted as Stachelhaus-code it is possible to predict and to change substrate specificities of a A domain in vitro, (Khurana et al. 2010, Rausch et al. 2005, Rottig et al. 2011, Kries et al. 2014). The most obvious disadvantage of this attempt is its inapplicability in vivo. One major reason for this drawback is that C domains also have selectivities resulting in substrate incompatibilities 10 (Belshaw et al. 1999).

A further attempt (WO200130985, Marahiel et al.) to vary known NRPS biosynthetic clusters is based on the exchange of single domains, didomains or whole modules and the knowledge of exactly defined borders (linkers) between individual domains. With this invention it was possible to alter just a few NRPSs successfully by introduction of additional modules or deleting them. However, it never was possible to produce totally artificial NRPSs from the artificial de novo combination of modules. This would result in new NRPS not present in nature that would produce also new peptides. The problem of such exchanges or combinations always was the uncertainty concerning the compatibility of modules and/or domains between each other. The shortcomings resulting from the lack of a solution 25 to the problem mentioned above is illustrated by the fact that almost no artificial peptides have been designed by this approach.

Another attempt (WO2007014076, Walsh et al.) to vary known NRPS biosynthetic clusters is based on mutagenesis of so called "assembly lines" other word for synthases. Mutagenesis of genes of NRPS is not subject matter of the present invention although the present inventive methods can be combined with a mutagenesis that will alter the generated NRPS and cause altered peptide synthesis. This mutagenesis could be useful for increasing the diversification of NRPS libraries and the NRPS clone numbers in the library.

Despite the modular organization of NRPSs, prior to this invention it has been very difficult to swap domains and/or modules resulting in active NRPSs not to mention the construction of complete NRPSs de novo.

SUMMARY OF THE INVENTION

NRPS and PKS is meant a polypeptide or plurality of interacting polypeptides that form multimodular enzymes which synthesize one or more of the following categories of small molecules: (i) nonribosomal peptides, (ii) polyketides, and (iii) nonribosomal peptide-polyketide hybrids. NRPS comprise an initiation module and a termination module. NRPS may further comprise one, two, three, four, five, six, seven, or more elongation modules. NRPS lines may be synthases, synthetases, or a combination thereof. By "assembly" is meant a set of domains. A plurality of assembly comprise an NRPS. One or more polypeptides may comprise a module.

Combinations of modules can catalyze a series of reactions to form larger molecules. In one example, a module may comprise a C (condensation) domain, an A (adenylation) domain, and a peptidyl carrier protein domain. For more structural information on A domains, didomains, domain-domain interfaces and complete modules see Conti et al. (1997), Sundlov et al. (2013), Tanovic et al. (2008), Mitchell et al. (2012) and Tan et al. (2015).

By "initiation module" is meant a module which is capable of providing a monomer to a second module (e.g., an elongation or termination module). In the case of an NRPS, an initiation module comprises, for example, an A (adenylation) domain and a PCP (peptidyl carrier protein) or T (thiolation) domain. The initiation module may also contain an E (epimerization) domain. In the case of a PKS, the initiation module comprises an δAT (acetyltransferase) domain and an acyl carrier protein (ACP) domain.

Initiation modules are preferably at the amino terminus of a polypeptide of the first module of an assembly line, and each assembly line preferably contains one initiation module.

By "elongation module" is meant a module which adds a monomer to another monomer or to a polymer. An elongation module may comprise a C (condensation), Cy (heterocyclization), E, MT (methyltransferase), Ox (oxidase), or Re (reductase) domain; an A domain; or a T domain. An elongation domain may further comprise additional E, Re, DH (dehydration), MT, NMet (N-methylation), AMT (Aminotransferase), or Cy domains.

By "termination module" is meant a module that releases the molecule (e.g., an NRP, PK, or combination thereof) from the assembly line. The molecule may be released by, for example, hydrolysis or cyclization. Termination modules may comprise a TE (thioesterase), C, or Re domain. The termination module is preferably at the carboxy terminus of a polypeptide of an NRPS or PKS. The termination module may further comprise additional enzymatic activities (e.g., oligomerase activity).

By "domain" is meant a polypeptide sequence, or a fragment of a larger polypeptide sequence, with a single enzymatic activity. Thus, a single polypeptide may comprise multiple domains. Multiple domains may form modules. Examples of domains include C (condensation), Cy (heterocyclization), A (adenylation), T (thiolation), TE (thioesterase), E (epimerization), MT (methyltransferase), Ox (oxidase), Re (reductase), KS (ketosynthase), AT (acyltransferase), KR (ketoreductase), DH (dehydratase), and ER (enoylreductase).

By "nonribsomally synthesized peptide," "nonribosomal peptide," or "NRP" is meant any polypeptide not produced by a ribosome. NRPs may be linear, cyclized or branched and contain proteinogenic, natural or non-natural amino acids, or any combination thereof. NRPs include peptides produced by an assembly line.

By "polyketide" is meant a compound comprising multiple ketyl units.

By "nonribosomal peptide synthetase" is meant a polypeptide or series of interacting polypeptide that produce a nonribosomal peptide.

By "polyketide synthase" (PKS) is meant a polypeptide or series of polypeptides that produce a polyketide. By "alter an amount" is meant to change the amount, by either increasing or decreasing. An increase or decrease may be by 3%, 5%, 8%, 10%, 15%, 20%, 30%, 40%, 50%, 60%, 70%, 80%, 90%, 100%, or more.

By "altering a structure" any change in a chemical (e.g., covalent or noncovalent) bond as compared to a reference structure is meant.

By "mutation" an alteration in the nucleic acid sequence such that the amino acid sequence encoded by the nucleic acid sequence has at least one amino acid alteration from a naturally occurring sequence is meant. The mutation may, without limitation, be an insertion, deletion, frameshift mutation, or a missense mutation. This term also describes a protein encoded by the mutant nucleic acid sequence.

By "variant" a polypeptide or polynucleotide with at least 10%, 20%, 30%, 40%, 50%, 60%, 70%, 80%, 90%, 95%, or 99% sequence identity to a reference sequence is meant. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications.

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{100}$ indicating a closely related sequence (Altschul et al., 1990).

Other features and advantages of the invention will be apparent from the following Detailed Description, the drawings, and the claims.

BRIEF DESCRIPTION OF THE DRAWINGS

The present invention provides methods for generating artificial NRPSs which have the ability to synthesis all desired natural occurring or artificial peptides. These artificial NRPSs composed by the present invention are useful for producing novel peptides having activities including but not limited to antimalarial, immunosupressory, antitumor, anticholestrolemic, antibiotic (e.g., antibacterial), and antifungal activities.

The problem of current available prior art methods has always been the uncertainty concerning the compatibility of modules and/or domains between each other. The reason for this drawback is that C domains also have selectivity which may lead to incompatibilities (Belshaw et al. 1999).

The present invention provides a reliable method of generating functional native, modified or artificial NRPSs available for the first time, by introducing the concept of "exchange-units". This concept provides simple rules for the design, cloning and production of non-ribosomal peptides (NRPs) of a desired AA composition, structure and length to adhere to.

Figure 4:
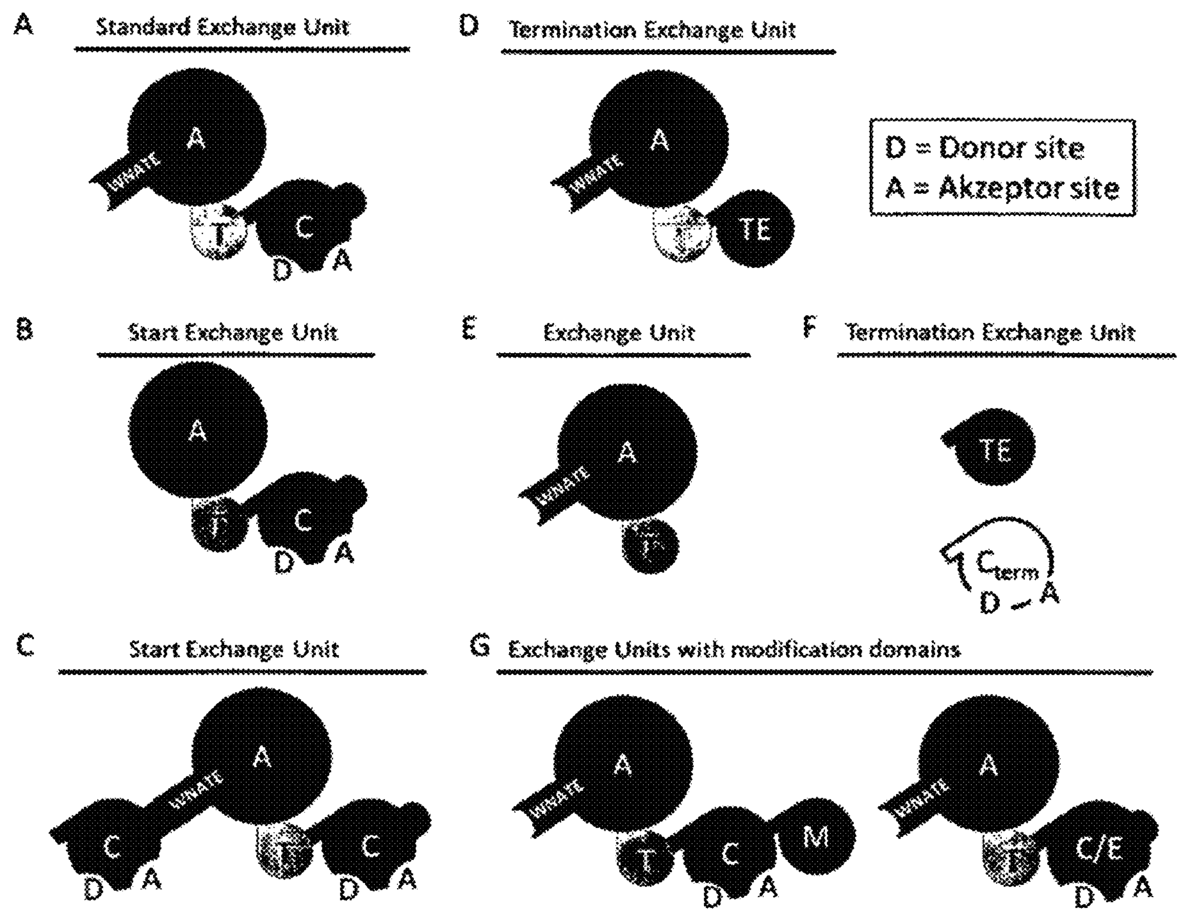

We were able to show that by fusing well-defined domain units in a defined sequential arrangement at accurately defined AAs in the regions coding for the linkers, called "exchange-units" (EUs) functional NRPSs can be constructed without impairing or loss of activity of said domains (FIG. 4).

General Architecture

A standard EU is defined as the composition of an A domain followed by a T and C domain. The first EU (start EU) sometimes possesses an additional C domain in front of the first NRPS A domain and the last (termination EU) is composed either of an A, T and TE domain or solely of a TE domain. In the latter case the EU next to the last EU is composed of an A and T domain. Additionally to the "standard domains" (C, A, T, TE) a Cy domain instead of a C domain and a Cterm domain in place of a TE domain can be present. Furthermore, modification domains like an E, MT domain or Ox domain can be included within the EUs.

EU Boarders

The boarders of standard EUs are defined by the consensus motive WNATE (amino acid code) within the C-A linkers. Linkers between NRPS domains previously were described by Marahiel et al. (WO2001130985). Every standard EU starts with the consensus motive WNATE, followed by A, T, C domains and stops with the AA in front of the N-terminal AA (W) of the next C-A linker consensus motive. A termination EU starts with the consensus motive WNATE, followed by an A, T and a TE or Cterm domain. If the termination EU, used for the design of the assembly line just consists of a TE or Cterm, the EU (A-T) next to this preferably ends with the last AA of the T domain.

Fusion of EUs

EUs, no matter of origin (bacteria, fungi, plants) can be used as building blocks according to the definition of EUs like a molecular construction kit, if the following rule according the concatenation of EUs is met. To prevent any problems concerning incompatibilities between EUs the substrate specificities of the C domain must be strictly adhered to. This means that the specificity of the A domain of the downstream EU always has to fit the substrate specificities of the upstream C domain. The assembly of EUs can be achieved by methods of molecular biology, like Gibson Cloning, Yeast based TAR-cloning et cetera.

The Preferred Embodiments of the Invention

A preferred embodiment of the invention is a method of generating NRPS containing an assembly of two or more exchange units (EU), comprising a EU encoding a polypeptide comprising an A domain followed by a T and a C domain.

Furthermore a method described above of wherein the first EU of the assembly has an additional C domain in front of the first A domain and/or wherein the last EU of the assembly is composed either of an A, T and TE domain and/or wherein the last EU of the assembly is a TE or $C_{term}$ domain and/or wherein the previous EU to the last EU of the assembly is composed of an A and T domain and/or wherein Cy domains can replace C domains.

Furthermore methods described above wherein modification domains as E, MT or Ox can be added to the EUs.

Another preferred embodiment of the invention is a method wherein the assembly of EUs is composed by EUs derived from species as but not limited to bacteria, fungi or plants and the substrate specificities from C domain from particular species and the A domain of the adjacent following EUs from a another species has to be the same or similar, wherein said bacterium is *Bacillus subtilis, Pseudomonas syringae, Streptomyces* sp., myxobacteria, cyanobacteria or *Escherichia coli* and wherein said fungi is *Aspergillus* sp., *Penicillium* sp. or *Fusarium* sp.

The assembly of the EUs can be achieved by methods of molecular biology as but not limited to Gibson cloning or Yeast based TAR-cloning.

A preferred requisite of all methods mentioned above is a defined consensus sequence Trp-Asn-Ala-Thr-Glu (WNATE) (SEQ ID NO: 1) between the borders of the EUs within the C-A linker.

The designed peptides might also be part of hybrids with polyketides, fatty acids or terpenes requiring the construction of hybrid enzymes (e.g. NRPS-PKS hybrids) which are also embodiment of the present invention. The NRPS can also be a PKS.

The number of EUs in an EU assembly can vary between 2-10 EU or 11-100 EUs.

Another preferred embodiment is a method for the identification and production of peptides. The activity of the peptides mentioned above can be but is not limited to antibiotic, antifungal, antineoplastic, or immunosuppressant.

According to the present invention, constructed peptides may be known peptides, derivatives thereof and non-natural peptides designed by computer aided molecular design or similar methods.

Also a kit composing genes encoding NRPS containing an assembly of EUs comprising a) the following EU domains A, T, C or b) an assembly of EUs containing modification domains as E, MT or Ox or c) an assembly of EUs containing as starting EU the domains C, A, T, C domains or d) an assembly of EUs containing as last EU the domains A, T or TE or e) an assembly of EUs containing instead of a C a Cy or $C_{term}$ or d) an assembly of EUs containing EUs from different species, wherein the adjacent C and A domains from different species must have the same or similar substrate specificity and e) the borders between the EUs are defined by the sequence Trp-Asn-Ala-Thr-Glu (SEQ ID NO: 1) within the C-A linker for performing the methods above is another preferred embodiment of the invention.

Another preferred embodiment are NRPS gene libraries produced by the Kit mention above. Said library comprises at least 15, or 25 or 50 or 100 or 1000 EUs encoding gene variants in each NRPS gene in the library.

Libraries of NRPS may be generated using molecular biology methods standard in the art. Other libraries of NRPS may be generated using molecular biology methods standard in the art followed by mutagenesis. Random mutagenesis of a domain or domains of an assembly line may be performed using known methods such as error prone PCR described herein. Mutating domains Mutagenesis may be accomplished by variety of means, including the GeneMorph<(R)> II EZClone Domain Mutagenesis Kit (Stratagene, La Jolla, Calif). Error prone PCR is a method standard in the art and described in Beaudry and Joyce {Science 257:635 (1992)) and Bartel and Szostak {Science 261: 1411 (1993)). This technique may be used to introduce random mutations into genes coding for proteins. Kits for performing random mutagenesis by PCR are commercially available, for example, the Diversify™ PCR Random Mutagenesis Kit (BD Biosciences, Mountain View, Calif.). Chemical mutation, radiation, and any other technique known in the art for modifying the nucleic acid sequence are appropriate for use in the present invention.

Example 1: Comparison of the Present Invention (Concept of EUs) and the German Patent Application No. 1999151196

Figure 5:
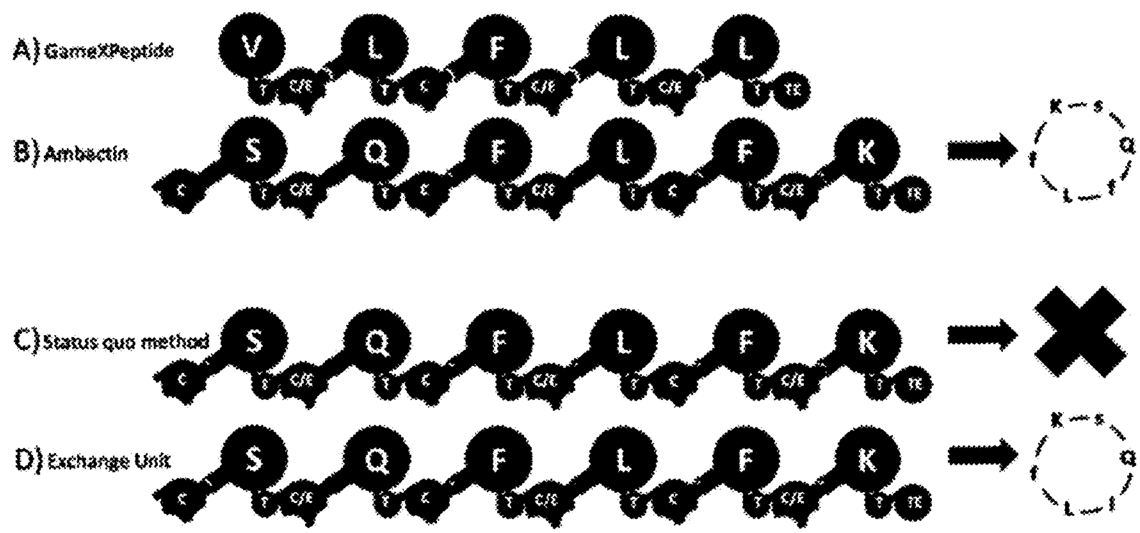

To compare the present invention with the status quo method, the following experiment was performed. In this experiment we tried to swap several 25 domains (yellow) in the Ambactin producing NRPS AmbS to produce a new Ambactin derivative (FIG. 5): on the one hand according to the concept of EUs FIG. 5D and on the other hand according to the state of the art method FIG. 5C suggested by Marahiel et al. (WO200130985). Only the present invention led to the desired cyclic peptide. The other recombinant NRPS FIG. 5C showed no production of any new derivatives.

Figure 6:
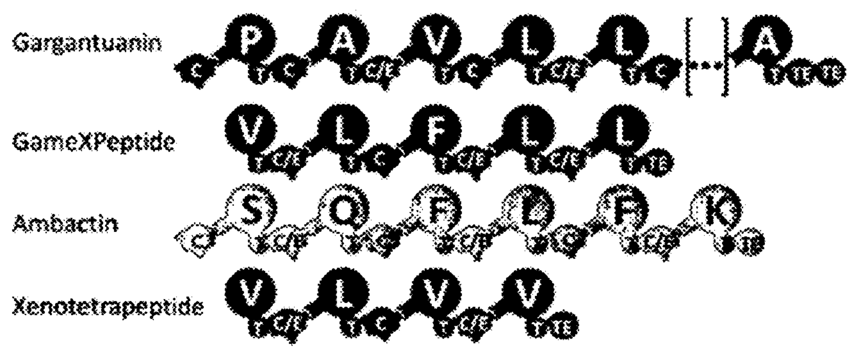

Example 2: De Novo Assembly of the NRPS Biosynthesis Cluster Plu3263 (GxpS) Responsible for the GameXPeptide Synthesis To support the accuracy of our invention we reassembled the GameXPeptide producing NRPS from known NRPS building blocks. As predicted this artificial NRPS is able to produce the desired peptide (FIG. 6).

Figure 7:
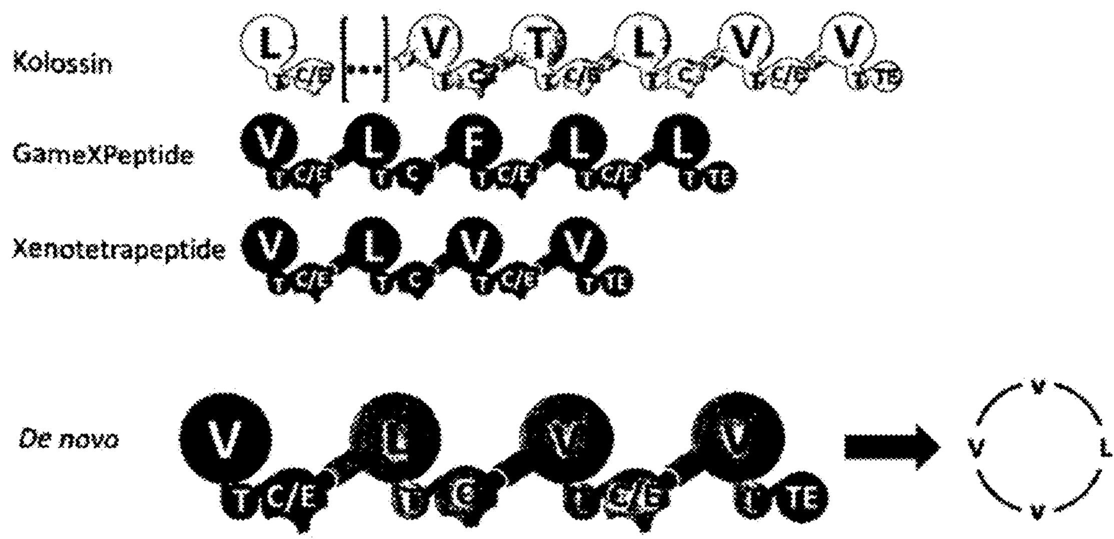
Figure 8:
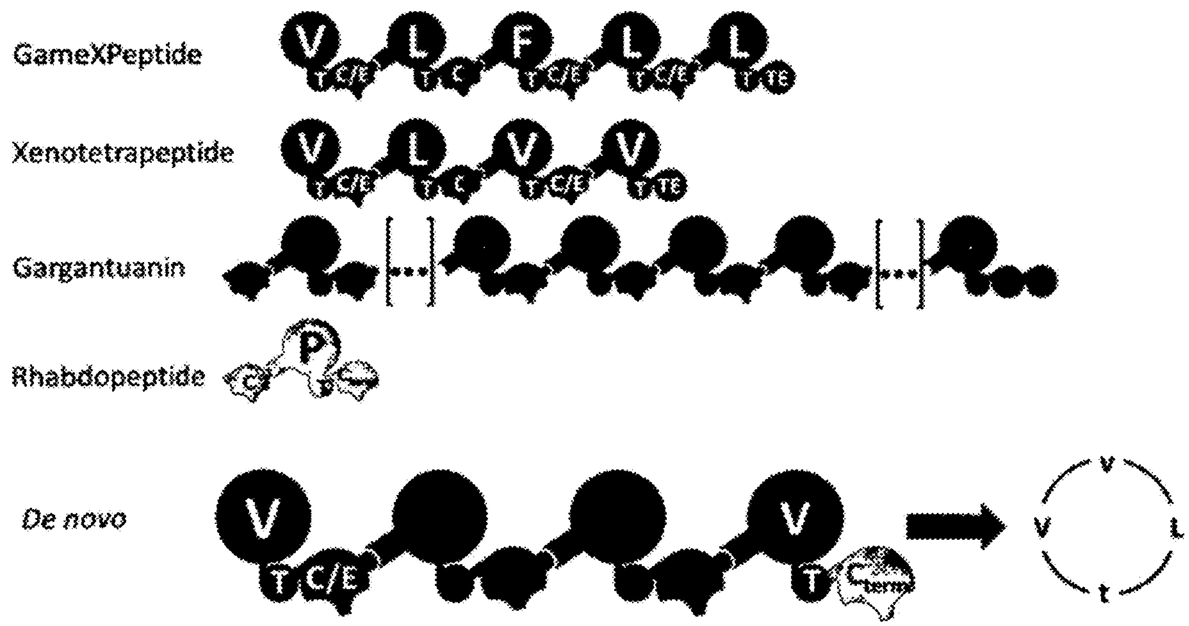

Example 3. De Novo Assembly of the NRPS Biosynthesis Cluster XtpS Responsible for the Xenotetrapeptide Synthesis and Production of a Threonine Containing Derivative To support the accuracy of our invention and its application to construct new and artificial NRPS producing novel peptides (De novo construction of XtpS FIG. 7, artificial NRPS FIG. 8).

Example 4: Recombination of EUs of Gram-Positive and Gram-Negative Origin

Figure 9:
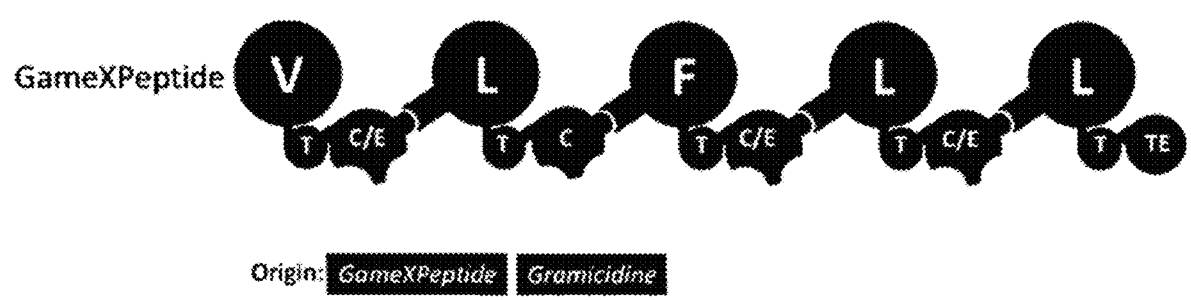

To show that our invention and the introduced rules are applicable ubiquitously, we recombined EUs from Gram-negative (*P. luminescens* TT01) and Gram-positive {*B. brevis* AJCC 999) bacteria. As expected this artificial NRPS is also able to produce the desired peptide (FIG. 9).

BRIEF DESCRIPTION OF THE DRAWINGS

FIG. 1

Schematic representation of a NRPS. The domains are colored: Adenylation (A, black), thiolation (T, light grey), condensation (C, grey), modification (M, dark grey), thioesterase (TE, dark grey). Donor (D) and acceptor (A) sites of the condensation domain.

FIG. 2

Schematic diagram of NRPS adenylation and peptidyl carrier protein.

Figure 1:
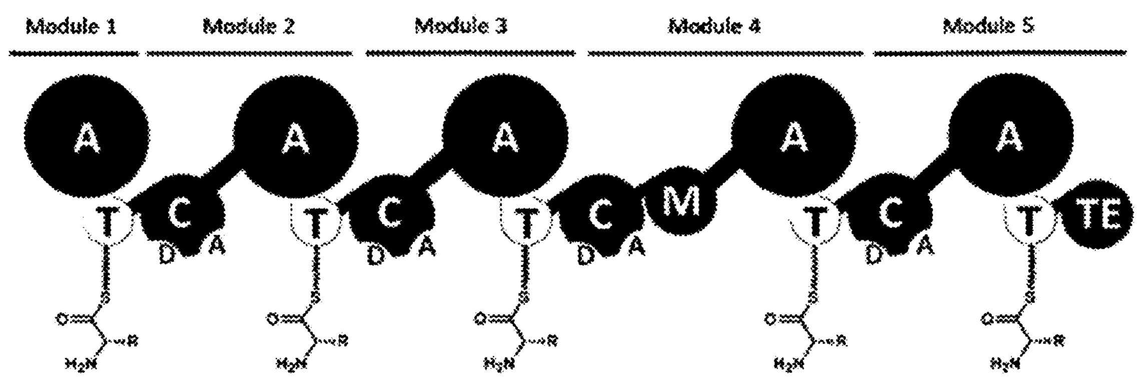
Figure 2:
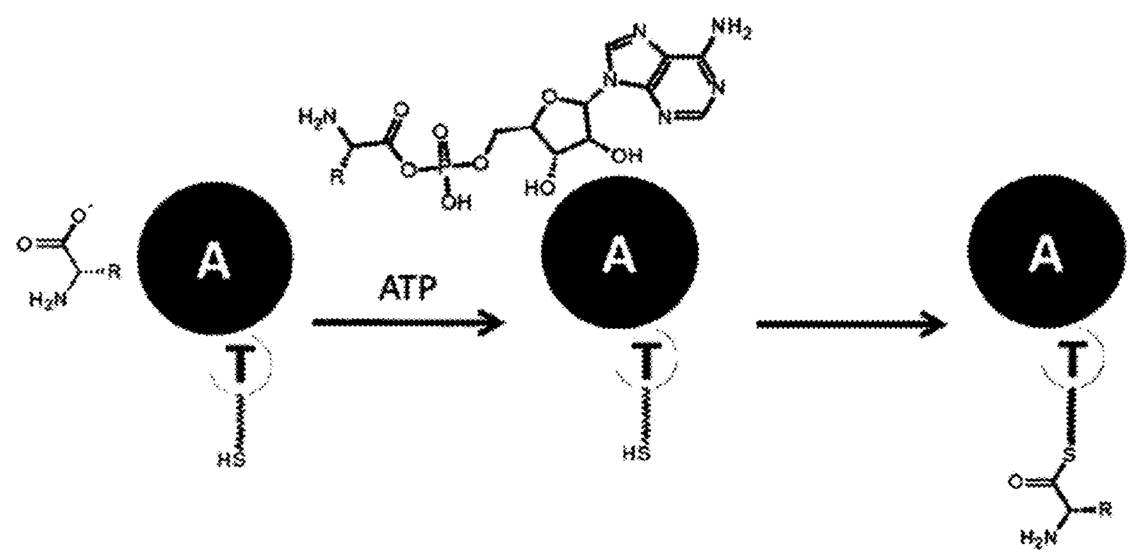
Figure 3:
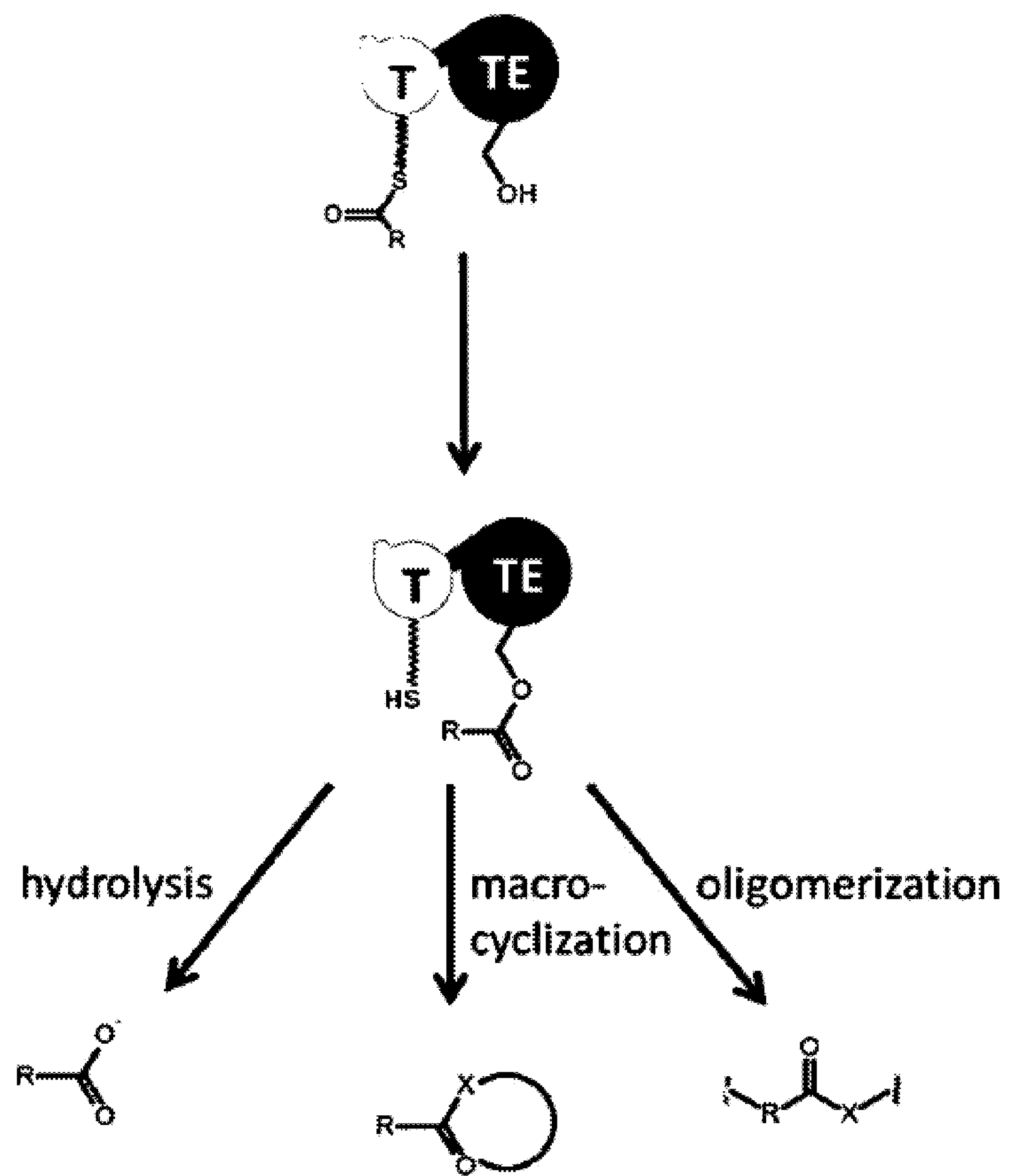

FIG. 3 Schematic diagram showing termination by the thioesterase domain (TE).

FIG. 4

Schematic representation of selected exchange units. The domains are highlighted and labeled: Adenylation (A, black), thiolation (T, light grey), condensation (C, grey), condensation dual (C/E, grey), modification (M, dark grey).

FIG. 5

Didomain and exchange unit swapping. Construction of a functional NRPS for the production of a cyclo(sQIUK) peptide. A: GameXPeptide, B: Ambactin, C: Status quo method (no production), D: Exchange Unit (production).

FIG. 6

De novo construction of a functional cyclo(vLfIL) peptide producing NRPS. The artificial NRPS is a combination of five EUs from four different NRPSs.

FIG. 7

Construction of a functional cyclo(vLvV) peptide producing NRPS. The recombined NRPS is a combination of five EUs from *P. luminescens* TT01 and *X. nematophila* ATCC 19061.

FIG. 8

De novo construction of a functional cyclo(vLtV) peptide producing NRPS. The recombined NRPS is a combination of five EUs from *P. luminescens* TT01*, X. bovienii* SS-2004 and *X. nematophila* ATCC 1906.

FIG. 9

Construction of a functional cyclo(vLfIL) peptide producing NRPS. The recombined NRPS is a combination of six EUs from *P. luminescens* TT01 (Gram-negative, black) and *B. brevis* ATCC 999 (Gram-positive, grey).

LITERATURE

S. F. Altschul, W. Gish, W. Miller, E. W. Myers, D. J. Lipman, J. Mol. Biol. 1990, 215(3), 403-410

M. Ishizuka, H. Takayama, T. Takeuchi, J. Antibiot. 1967, 20, 15-24.

P. Khurana, R. S. Gokhale, D. Mohanty, BMC Bioinformatics 2010, 11, 57

H. Kries, R. Wachtel, A. Pabst, B. Wanner, D. Niquille, D. Hilvert, Angew. Chem. Int. Ed. 2014, 53, 10105-10108.

L. L. Ling, T. Schneider, A. J. Peoples, A. L. Spoering et al., Nature 2015, 577, 445-459.

U. Linne, Daniel B. Stein, H. D. Mootz, M. A. Marahiel, Biochemistry 2003, 25 42, 5114-5124

W. Loeffler, J. Tschen, N. Vanittanakom, J. Phytopathol. 1986, 115, 204-213.

M. A. Marahiel, Chem. Biol. 1997, 4, 561-567.

R. McDaniel, A. Thamchaipenet, C. Gustafsson, F. Hong, M. Betlach, M. C. A. Mitchell, C. Shi, C. C. Aldrich, A. M. Gulick, Biochemistry 2012, 51, 3252-3263

C. Rausch, T. Weber, O. Kohlbacher, W. Wohlleben, D. H. Huson, Nuc. Acids. Res. 2005, 33, 5799-5808.

M. Rottig, M. H. Medema, K. Blin, T. Weber, C. Rausch, O. Kohlbacher, Nuc. Acids. Res. 2011, 39, W362-W367.

S. A. Sieber, M. A. Marahiel, Chem. Rev. 2005, 105, 715-738.

S. Smith, S. Tsai, Nat. Prod. Rep. 2007, 24, 1041-1072.

T. Stachelhaus, H. D. Mootz, M. A. Marahiel, Chem. Biol. 1999, 6, 493-505.

T. Stachelhaus, A. Schneider, M. A. Marahiel, Science 1995, 269, 69-72 J. A. Sundlov, A. M. Gulick, Acta Cryst. 2013, D69, 1482-1492

X. Tan, Y. Dai, K. Zhou, Y. Jiang, Y. Ren, Y. Chen, C. Zhou, Acta Cryst. 2015, D71, 873-881

A. Tanovic, S. A. Samel, L. Essen, M. A. Marahiel, Science 2008, 321, 659-663

SEQUENCE LISTING

<160> NUMBER OF SEQ ID NOS: 1

<210> SEQ ID NO 1
<211> LENGTH: 5
<212> TYPE: PRT
<213> ORGANISM: Artificial
<220> FEATURE:
<223> OTHER INFORMATION: Sequence in the bridging linkers between EU modules

<400> SEQUENCE: 1

Trp Asn Ala Thr Glu
1 5

D. P. Bartel, J. W. Szostak, Science 1993, 261, 1411-1418

A. A. Beaudry, G. F. Joyce, Science 1992, 257, 635-641

P. J. Belshaw, C. T. Walsh, T. Stachelhaus, Science 1999, 284, 486-9-489

Betlach, G. Ashley, Proc. Nat. Acad. Sci. USA 1999, 96, 1846-1841

D. E. Cane, C. T. Walsh, C. Khosla, Science 1998, 282, 63-68.

E. Conti, T. Stachelhaus, M. A. Marahiel, P. Brick, EMBO J. 1997, 16, 4174-83.

E. A. Emmel, C. L. Verweij, D. B. Durand, K. M. Higgins, Science 1989, 246, 1617-1620.

K. Eppelmann, T. Stachelhaus, M. A. Marahiel, Biochemistry 2002, 41, 9718-9726

What is claimed is:

1. A method of generating a non-ribosomal peptide synthetase (NRPS) comprising:

assembling an assembly of three or more exchange units (EU), said assembly including a first EU and a last EU, wherein each EU comprises an adenylation (A) domain followed by a thiolation (T) domain and a condensation (C) domain, wherein adjacent exchange units are connected by a linker (C-A linker) between the condensation (C) domain of an EU and the adenylation (A) domain of the adjacent EU and said C-A linker includes a consensus sequence Trp-Asn-Ala-Thr-Glu (SEQ ID NO: 1);

wherein each EU optionally further comprises an epimerization (E) domain, N-methylation (MT) domain, oxidation (Ox) domain, or other NRPS domain;

wherein the first EU of the assembly optionally further comprises an additional condensation (C) domain in front of the first adenylation (A) domain;

wherein the last EU is optionally an adenylation (A) domain, a thiolation (T) domain, or a thioesterase (TE) domain;

wherein within an individual EU the condensation (C) domain is optionally replaced by a heterocyclization (Cy) domain or a terminal condensation ($C_{term}$) domain; and wherein said assembly optionally contains EUs from different species and adjacent C and A domains from different species have the same or similar substrate specificity.

2. The method of claim 1, wherein the first EU of the assembly has an additional condensation (C) domain in front of the first A domain.

3. The method of claim 1, wherein the last EU of the assembly is composed either of an A domain, a T domain, or a TE domain.

4. The method of claim 1, wherein the last EU of the assembly is a TE domain.

5. The method of claim 4, wherein the previous EU to the last EU of the assembly is composed of an A and a T domain.

6. The method of claim 1, wherein in at least one EU a Cy domain or $C_{term}$ domain replaces the C domain.

7. The method of claim 1, wherein in at least one EU an E, MT, or Ox domain is added to the EU.

8. The method of claim 1, wherein the assembly of EU comprises EU domains derived from species of bacteria, fungi, and plants.

9. The method of claim 8, wherein the substrate specificity of the C domain from one species and the substrate specificity of the A domain of the next EU from a different species is the same or is related.

10. The method of claim 1, wherein assembling of the EUs is performed Gibson cloning or Yeast based TAR-cloning.

11. The method of claim 1, wherein the NRPS contains polyketides (PKs) EUs or NRPS-PKS EUs.

12. The method of claim 1, wherein the NRPS contains 3-10 EUs.

13. The method of claim 1, wherein the NRPS contains 11-100 EUs.

14. The method of claim 8, wherein said bacteria species are selected from *Bacillus subtilis, Pseudomonas syringae, Streptomyces* sp., or *Escherichia coli*. and wherein said fungi species are selected from yeast cells.

15. The method of claim 1 for the identification and production of peptides with activity as antibiotic, antifungal, antineoplastic agent, or immunosuppressant.

16. A kit comprising one or more genes each encoding a non-ribosomal peptide synthetase, wherein each of said one or more genes encodes an assembly of three or more exchange units (EU), said assembly including a first EU and a last EU, wherein each EU comprises an adenylation (A) domain followed by a thiolation (T) domain and a condensation (C) domain, wherein adjacent exchange units are connected by a linker (C-A linker) between the condensation (C) domain of an EU and the adenylation (A) domain of the adjacent EU and said C-A linker includes a consensus sequence Trp-Asn-Ala-Thr-Glu (SEQ ID NO: 1);

wherein each EU optionally further comprises an epimerization (E) domain, N-methylation (MT) domain, oxidation (Ox) domain, or other NRPS domain;

wherein the first EU of the assembly optionally further comprises an additional condensation (C) domain in front of the first adenylation (A) domain;

wherein the last EU is optionally an adenylation (A) domain, a thiolation (T) domain, or a thioesterase (TE) domain;

wherein within an individual EU the condensation (C) domain is optionally replaced by a heterocyclization (Cy) domain or a terminal condensation ($C_{term}$) domain; and wherein said assembly optionally contains EUs from different species and adjacent C and A domains from different species have the same or similar substrate specificity.

17. A non-ribosomal peptide synthetase gene library comprising a plurality of genes encoding non-ribosomal peptide synthetases, wherein each gene encodes an assembly of at least 15 exchange units (EUs), said assembly including a first EU and a last EU, wherein each EU comprises an adenylation (A) domain followed by a thiolation (T) domain and a condensation (C) domain, wherein adjacent exchange units are connected by a linker (C-A linker) between the condensation (C) domain of an EU and the adenylation (A) domain of the adjacent EU and said C-A linker includes a consensus sequence Trp-Asn-Ala-Thr-Glu (SEQ ID NO: 1);

wherein each EU optionally further comprises an epimerization (E) domain, N-methylation (MT) domain, oxidation (Ox) domain, or other NRPS domain;

wherein the first EU of the assembly optionally further comprises an additional condensation (C) domain in front of the first adenylation (A) domain;

wherein the last EU is optionally an adenylation (A) domain, a thiolation (T) domain, or a thioesterase (TE) domain;

wherein within an individual EU the condensation (C) domain is optionally replaced by a heterocyclization (Cy) domain or a terminal condensation ($C_{term}$) domain; and wherein said assembly optionally contains EUs from different species and adjacent C and A domains from different species have the same or similar substrate specificity.

18. The non-ribosomal peptide synthetase gene library of claim 17, wherein said each gene of said library encodes an assembly at least 25 EUs.

19. A non-ribosomal peptide synthetase gene of claim 17, wherein said each gene of said library encodes an assembly of at least 50 EUs.

20. A non-ribosomal peptide synthetase gene library of claim 17, wherein each gene of said library encodes an assembly of at least 100 EUs.

21. A non-ribosomal peptide synthetase gene library of claim 17, wherein diversity is increased by random mutagenesis.

22. A method of generating a non-ribosomal peptide synthetase (NRPS) comprising a step of:

assembling an assembly having only two exchange units (EU), a first EU and a second EU, wherein each of the two exchange units comprises an adenylation (A) domain followed by a thiolation (T) domain and a condensation (C) domain, wherein the two exchange units are connected by a linker (C-A linker) between the condensation (C) domain of the first EU exchange units and the adenylation (A) domain of the second EU, and said C-A linker includes a consensus sequence Trp-Asn-Ala-Thr-Glu (SEQ ID NO: 1);

wherein each EU optionally further comprises an epimerization (E) domain, N-methylation (MT) domain, oxidation (Ox) domain, or other NRPS domain;

wherein the first EU of the assembly optionally further comprises an additional condensation (C) domain in front of the first adenylation (A) domain;

wherein the second EU is optionally an adenylation (A) domain, a thiolation (T) domain, or a thioesterase (TE) domain;

wherein within an individual EU the condensation (C) domain is optionally replaced by a heterocyclization (Cy) domain or a terminal condensation ($C_{term}$) domain; and wherein said EUs are optionally from different species and adjacent C and A domains from different species have the same or similar substrate specificity.

* * * * *